United States Patent
Song et al.

(10) Patent No.: US 8,623,290 B2
(45) Date of Patent: *Jan. 7, 2014

(54) COLOR-CHANGING MATERIALS AND MULTIPLE COMPONENT MATERIALS HAVING A COLOR-CHANGING COMPOSITION

(75) Inventors: Xuedong Song, Alpharetta, GA (US); Kaiyuan Yang, Cumming, GA (US); Stephanie M. Martin, Woodstock, GA (US); Maia Bageant, Roswell, GA (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/602,556

(22) Filed: Sep. 4, 2012

(65) Prior Publication Data

US 2012/0328485 A1 Dec. 27, 2012

Related U.S. Application Data

(63) Continuation of application No. 12/503,398, filed on Jul. 15, 2009, now Pat. No. 8,273,306.

(51) Int. Cl.
 *G01N 31/22* (2006.01)

(52) U.S. Cl.
 USPC ........... 422/400; 436/164; 436/169; 604/358; 604/361

(58) Field of Classification Search
 USPC ........... 422/420, 400; 436/164, 169; 604/358, 604/361
 See application file for complete search history.

(56) References Cited

U.S. PATENT DOCUMENTS

| | | | |
|---|---|---|---|
| 4,231,370 A | 11/1980 | Mroz et al. | |
| 4,287,153 A | 9/1981 | Towsend | |
| 4,931,051 A | 6/1990 | Castello | |
| 5,035,691 A | 7/1991 | Zimmel et al. | |
| 5,302,654 A | 4/1994 | Ishii et al. | |
| 5,464,470 A | 11/1995 | Brachman et al. | |
| 6,121,509 A | 9/2000 | Ashraf et al. | |
| 6,756,520 B1 | 6/2004 | Krzysik et al. | |
| 6,772,708 B2 | 8/2004 | Klofta et al. | |
| 6,855,434 B2 | 2/2005 | Romasn-Hess et al. | |
| 7,005,557 B2 | 2/2006 | Klofta et al. | |
| 7,094,464 B2 | 8/2006 | Mao et al. | |
| 7,159,532 B2 | 1/2007 | Klofta et al. | |
| 7,306,764 B2 | 12/2007 | Mody | |
| 7,332,642 B2 | 2/2008 | Liu | |
| 8,273,306 B2 * | 9/2012 | Song et al. | 422/420 |
| 2002/0155281 A1 | 10/2002 | Lang et al. | |
| 2005/0112151 A1 | 5/2005 | Horng | |
| 2005/0234414 A1 | 10/2005 | Liu | |
| 2005/0234415 A1 | 10/2005 | Liu | |
| 2006/0229578 A1 | 10/2006 | Roe et al. | |
| 2007/0002072 A1 | 1/2007 | Frensch et al. | |
| 2007/0079748 A1 | 4/2007 | Ahmed | |
| 2007/0100305 A1 | 5/2007 | Isogai et al. | |
| 2008/0068399 A1 | 3/2008 | Goss et al. | |
| 2009/0275908 A1 | 11/2009 | Song | |
| 2011/0015063 A1 | 1/2011 | Gil et al. | |
| 2011/0015597 A1 | 1/2011 | Gil et al. | |
| 2011/0015599 A1 | 1/2011 | Song et al. | |

FOREIGN PATENT DOCUMENTS

| | | |
|---|---|---|
| KR | 10-1996-0014278 A | 5/1996 |
| KR | 10-2007-0083314 A | 8/2007 |
| KR | 10-2009-0061633 A | 6/2009 |
| KR | 10-2009-0074223 A | 6/2009 |
| WO | WO 2002/036177 A2 | 5/2002 |
| WO | WO 2008/038654 A1 | 4/2008 |
| WO | WO 2009/141684 A1 | 11/2009 |

* cited by examiner

*Primary Examiner* — Monique Cole
(74) *Attorney, Agent, or Firm* — Denise L. Stoker

(57) ABSTRACT

The present invention relates to a color-changing material and to a multiple-component material that includes a color-changing composition. The color-changing materials and color-changing compositions are capable of changing color in order to indicate a change in condition, such as a change in pH. The color-changing materials and color-changing compositions include a hydrogel-forming composition, a charged colorant and a pH adjuster. The hydrogel-forming composition includes at least one charged species.

22 Claims, No Drawings

COLOR-CHANGING MATERIALS AND MULTIPLE COMPONENT MATERIALS HAVING A COLOR-CHANGING COMPOSITION

This application claims priority as a continuation of application Ser. No. 12/503,398, filed on Jul. 15, 2009 now U.S. Pat. No. 8,273,306. The entirety of application Ser. No. 12/503,398 is incorporated herein by reference.

FIELD OF THE INVENTION

The present invention relates to color-changing materials that include a hydrogel-forming composition, a charged colorant, a pH adjuster and a solvent. The hydrogel-forming composition includes either (1) a charged hydrogel-forming polymer or (2) a neutral hydrogel-forming polymer and at least one of a charged polymer or a charged particle. The present invention also relates to multiple-component materials that include a substrate and a hydrogel layer formed on the substrate. The hydrogel layer includes a color-changing composition. The color-changing composition can cause the hydrogel layer to change in appearance of its color when the hydrogel layer is exposed to a change in physical or chemical environment. For example, the hydrogel layer may be on a nonwoven material that is used as a component of an absorbent article. The color-changing composition includes a hydrogel-forming composition, a charged colorant and a pH adjuster that changes color in response to the presence of urine and water. Further, the present invention relates to a method of printing on a substrate. The method includes the steps of providing a substrate to be printed upon and applying an ink material onto the substrate. The ink material includes a hydrogel-forming composition, a charged colorant, a pH adjuster and a solvent.

BACKGROUND OF THE INVENTION

Many products, including consumer and professional products, are more effectively used by an end user when they include a feature that indicates a particular condition or degree of use. An example of a visual indicator is a color indicator. Color indicators can either indicate a change in condition or a degree of use through a change from "no color" to "color" (or vice versa) or through a change from one color to a different color.

Exemplary conditions that could be monitored using a color indicator include physical conditions such as the presence of moisture and chemical conditions such as a change in pH. Exemplary consumer products that could be more effective and deliver more benefits to end users by incorporating a suitable color indicator include absorbent articles, facial tissues, bath tissue, paper towels, household cleaning items and personal cleaning wipes. Exemplary professional products that could be more effective and deliver more benefits to end users by incorporating a suitable color indicator include products for medical use, safety garments, industrial cleaning products and nonwoven materials.

Color indicators are well known and are available in various forms. Desirable performance attributes include durability and good retention (i.e. the color indicator remains where intended and does not leach out into other components of the product within which it is being used). Depending on the product application, it may also be desirable to have the structure in which the color indicator is used be wettable, but water insoluble. For purposes of applying the color indicator to a component of a product, it may also be desirable to have a color indicator that can be applied in liquid form at room temperature. When the color indicator is in a liquid form at room temperature, the color indicator can be printed (just like an ink composition) onto the desired component of a product.

Examples of how color indicators are already incorporated into consumer products include diapers that have wetness sensors. Some of the wetness sensors used in diapers change color to indicate wetness while others lose color in response to wetness (i.e. the color fades or disappears when it is dissolved by water). The concept of incorporating a color-changing composition into a wearable article (such as a disposable diaper) is known in the art. For example, U.S. Pat. No. 7,159,532 issued to Klofta et al. (hereinafter "the '532 patent") is directed to wetness indicating compositions having improved colorant retention and durability for use with wearable articles. The wetness indicating compositions of the '532 patent have a first binding agent and a second binding agent. The first binding agent immobilizes a colorant when the colorant is in its initial color state and the second binding agent immobilizes the colorant when the colorant is in its final color state. The component materials used in the examples provided in the '532 patent are solid at room temperature as indicated by the description that they need to be melted in order to combine them. While the wetness indicating compositions of the '532 patent are capable of changing color in response to a stimulus, they are not capable of being applied to an article in liquid form at room temperature.

While the color-changing compositions known in the art provide certain benefits, there remains a need for a film-forming composition that can be applied to a substrate. There also remains a need for a composition that is durable, has good retention and that shows rapid and dramatic color change when the composition is used in a product. When the purpose of the composition is to detect the presence of wetness, there remains a need for a composition that is water-resistant and water-insoluble. Further, there remains a need for a composition that can be applied, such as by printing, at room temperature so that the composition can be applied to a substrate without heating.

SUMMARY OF THE INVENTION

The present invention is directed to a color-changing material that includes a hydrogel-forming composition containing at least one charged species, a charged colorant, a pH adjuster and a volatile solvent. The hydrogel-forming composition is from 5 to 50% of the color-changing material. The charged colorant is from 0.1 to 10% of the color-changing material. The pH adjuster is from 0.001 to 10% of the color-changing material and the volatile solvent is from 50 to 90% of the color-changing material. The hydrogel-forming composition includes either a charged, hydrogel-forming polymer or a neutral, hydrogel-forming polymer. When a neutral, hydrogel-forming polymer is used, the hydrogel-forming composition also includes at least one charged species, such as a charged polymer or charged particle. Therefore, the charged species is either a charged, hydrogel-forming polymer, another type of charged polymer or a charged particle. For example, the hydrogel-forming composition can include a combination of a charged, hydrogel-forming polymer and a neutral hydrogel-forming polymer. Hydrogel-forming compositions are used for a wide variety of products, including hair gels. The hydrogel-forming compositions of the invention desirably have a highly-charged element to bind strongly with an oppositely-charged colorant. The charged, hydrogel-forming polymers desirably have low water solubility, but can be either dissolved or suspended well in an aqueous solution or in a mixture of organic solvent and water. The color-changing material is liquid at room temperature. When the color-changing material is applied to a surface, such as a substrate, the color-changing material can be applied at room temperature (without heating) to form a hydrogel layer on the substrate. After the color-changing material is applied to a substrate, the volatile solvent evaporates.

In another aspect, the present invention is directed to a multiple-component material. The multiple-component material includes a substrate and a hydrogel-forming layer. The hydrogel-forming layer includes a color-changing composition. The color-changing composition includes a hydrogel-forming composition having at least one charged species, a charged colorant and a pH adjuster. The hydrogel-forming composition includes either a charged, hydrogel-forming polymer or a neutral, hydrogel-forming polymer. When the hydrogel-forming composition includes a neutral, hydrogel-forming polymer, the composition also includes either a charged polymer or a charged particle. For the multiple-component material, the hydrogel-forming layer is formed on the substrate in one or more patterns selected from stripes, dots, geometric shapes, irregular shapes, alpha-numeric characters, anthropomorphic images, pictorial representation of animals, pictorial representation of inanimate objects, cartoon characters, logos and trademarks. The multiple-component material may be incorporated into various articles, including disposable absorbent articles such as incontinence garments. For example, the multiple-component material may be incorporated into or form the outer cover of a disposable diaper. In this use as part of a disposable diaper, the multiple-component material can be used to indicate a change in the condition of the disposable diaper, such as the presence of urine or other waste. The charged colorant in the color-changing composition can be a pH indicator. The color-changing compositions can include more than one charged colorant.

In another aspect, the present invention relates to a method of printing on a substrate. The method includes a step of providing a substrate to be printed upon. The substrate may be a woven or a nonwoven material. The substrate may also be a laminate of a nonwoven material and a film, such as a polyolefin film. The method also includes step of applying an ink material onto the substrate. The ink material includes a hydrogel-forming composition having at least one charged species, a charged colorant, a pH adjuster and a volatile solvent. As the ink material dries on the substrate, the volatile solvent evaporates and the remaining components of the ink material form a hydrogel layer on the substrate. The ink material is liquid at room temperature to permit easy application to the substrate. In addition to being printed on the substrate, the ink material may also be stamped on the substrate.

These aspects and additional aspects of the invention will be described in greater detail herein. Further, it is to be understood that both the foregoing general description and the following detailed description are exemplary and are intended to provide further explanation of the invention claimed.

DETAILED DESCRIPTION OF THE INVENTION

The present disclosure of the invention will be expressed in terms of its various components, elements, constructions, configurations, arrangements and other features that may also be individually or collectively be referenced by the term, "embodiment(s)" of the invention, or other similar terms. It is contemplated that the various forms of the disclosed invention may incorporate one or more of its various features and embodiments, and that such features and embodiments may be employed in any desired, operative combination thereof.

It should also be noted that, when employed in the present disclosure, the terms "comprises", "comprising" and other derivatives from the root term "comprise" are intended to be open-ended terms that specify the presence of any stated features, elements, integers, steps, or components, and are not intended to preclude the presence or addition of one or more other features, elements, integers, steps, components, or groups thereof.

The present invention relates to color-changing materials and multiple-component materials that include a color-changing composition. Unlike prior art color-changing materials, the color-changing materials of the present invention are either single-phase fluids or two-phase particle suspensions in a fluid. The color-changing materials and color-changing compositions include a solution medium, such as a volatile solvent, are liquid at room temperature and therefore, can be applied to a substrate without heating. For example, the color-changing materials and color-changing compositions may be printed like an ink onto a substrate at room temperature. This feature of the color-changing materials and color-changing compositions makes them easier to handle during the manufacture of the articles to which they are applied. Further, the color-changing materials and color-changing compositions of the present invention form a film when they are applied, such as by printing, to a substrate and dried. A benefit of forming a film on the substrate is to afford good adherence and to prevent cracking.

The color-changing materials and color-changing compositions of the invention are dissolved in a solution, such as a volative solvent, as a vehicle for the materials and compositions to be applied to a substrate where the solvent portion of the solution evaporates after application. When they form a film-like hydrogel-forming layer on a substrate (after evaporation of the solvent), the color-changing materials and color-changing compositions of the invention are wettable but insoluble in water. This feature makes the color-changing materials and color-changing compositions desirable for use in articles where the compositions will be exposed to wetness. The feature also results in color-changing materials and color-changing compositions that are durable and that are resistant to leaching away from the substrates to which they are applied. The hydrogel-forming layer may be formed on a substrate in a desired pattern including stripes, dots, geometric shapes and irregular shapes and combinations of such pattern elements. The hydrogel-forming layer may also be formed on the substrate as an alpha-numeric character, an anthropomorphic image, a pictorial representation of an animal, a pictorial representation of an inanimate object, a cartoon character, a product or company logo and a trademark or brand or combinations of such pictorial elements.

The present invention is directed to a color-changing material that includes a hydrogel-forming composition, a charged colorant, a pH adjuster and a volatile solvent. The hydrogel-forming composition includes at least one charged species, such as a charged, hydrogel-forming polymer and/or charged particles. The hydrogel-forming composition can include a charged, hydrogel-forming polymer by itself. When the hydrogel-forming composition includes a neutral hydrogel-forming polymer, the hydrogel-forming composition also includes a charged polymer or charged particle. The hydrogel-forming composition can also include a combination of a charged, hydrogel-forming polymer and a neutral hydrogel-forming polymer. Hydrogel-forming compositions are used for a wide variety of products, including hair gels. The hydrogel-forming compositions of the invention have the highly-charged species to bind strongly with an oppositely-charged colorant. The highly-charged species can be the charged, hydrogel-forming polymer, the charged particles or combinations of such polymers and particles.

The charged, hydrogel-forming polymers desirably have low water solubility, but can be either dissolved or suspended well in an aqueous solution or a mixture of organic solvent and water. The charged, hydrogel-forming polymers may be branched, linear or cross-linked and they may be copolymers, such as block copolymers. The charged, hydrogel-forming polymers may be pre-formed or formed in situ from certain monomers. The in-situ formation of the charged, hydrogel-forming polymers may be triggered by a number of techniques such as photon induction and use of free radicals. Examples of suitable charged, hydrogel-forming polymers include poly(ethylene glycol)-grafted cationic hydrogels (such as those described in the publication, K. Podual, F. J. Doyle III, and N. A. Peppas, Biomaterials, 21, 1439-1450, 2000); the copolymer formed from 2-hydroxy methacrylate (HEMA) and methacrylamide propyltrimethylammonium chloride; and dehydroxanthan gum (such as AMAZE XT film former commercially available from AkzoNobel). Additional examples of suitable charged, hydrogel-forming polymers include the crosslinked cationic copolymer of vinylpyrrolidone (VP) and 3-dimethylaminopropyl(meth)acrylamide (DMAPMA) monomer; (3-acrylamidopropyl)-trimethylammonium chloride (APTMAC1) monomer crosslinked with a neutral crosslinker (N,N-methylenebisacrylamide); crosslinked hydrophobically-modified dialkylallylammonium salts; vinyl ether of monoethanolamine; and copolymerization of N,N,N,N-tetraallyl piperazinium dibromide (TAP) with N, N diallyl morpholinium bromide (DAM). The hydrogel-forming composition ranges from 5% to 50% of the color-changing material or the color-changing composition. If a charged, hydrogel-forming polymer is used in the hydrogel-forming composition, the polymer ranges from 5% to 50% of the hydrogel-forming composition.

Examples of suitable neutral, hydrogel-forming polymers include polyethylene oxide, polyAMPS, polyvinylpyrrolidone, polyacrylamide, polyvinyl alcohol, sodium polyacrylate, agarose, methylcellulose and hylaronan. The neutral hydrogel-forming polymer can ranges from 5% to 50% of the hydrogel-forming composition.

Examples of suitable charged (either positively or negatively charged) particles include resin particles, including ion exchange resins such as REILLEX HPQ ion-exchange resin (a poly(4-vinylpyridine), cross-linked, methyl chloride quaternary salt) commercially available from Reilly Industries, Inc. and sold through Sigma-Aldrich. Other examples of charged particles include latex particles made of polystyrenes and polymethylacrylates that have surface functional groups to allow covalent attachment of the charged colorants. Additionally, inorganic particles such as clays and zeolites that allow absorption of oppositely-charged charged colorants may be used as charged particles. The charged particles may be solid or porous. Charged particles that are porous may be desirable when it is necessary to absorb/adsorb a greater quantity of charged colorant. The size of the charged particles may range from 10 nanometers to 10 micrometers and desirably from 500 nanometers to 10 nanometers. The color-changing materials and color-changing compositions of the invention include charged particles in an amount of from 0.1% to 10% of the total weight of the color-changing material or color-changing composition. Desirably, the color-changing materials and color-changing compositions of the invention include charged particles in an amount of from 0.5% to 5% of the total weight of the color-changing material or color-changing composition.

Desirably, the charged particles have a large surface area on which the charged colorant can be non-diffusively immobilized. The charged colorant may be covalently attached to or may be physically adsorbed onto the surface of the particles. The stable absorption of the charged colorant onto the charged particles increases the stability of the charged colorant and reduces leaching of the charged colorant out of the color-changing material or color-changing composition.

In one aspect, the present invention is directed to a multiple-component material that includes a substrate and a hydrogel-forming layer. The substrate may be in the form of a porous foam, a reticulated foam, cellulose tissues, a plastic film, a woven material or a nonwoven material. Suitable plastic films that may be used to form the substrate include polyethylene films and polypropylene films. Suitable woven materials include woven materials made from natural fibers, synthetic fibers or combinations of natural and synthetic fibers. Natural fibers include cotton, silk and wool fibers and synthetic fibers include polyester, polyethylene and polypropylene fibers. Suitable nonwoven materials include nonwoven materials made through traditional techniques such as spunbond, meltblown and bonded carded web materials. The spunbond, meltblown and bonded carded web materials may be made from suitable synthetic fibers such as polyester, polyethylene and polypropylene fibers. The substrate may include combinations of the materials identified above such as a substrate that includes both a porous foam and a nonwoven material or a substrate that includes both a plastic film and a nonwoven material.

The multiple-component materials of the invention also include a hydrogel-forming layer that is adhered to the substrate. The hydrogel-forming layer includes a color-changing composition. The color-changing composition includes a hydrogel-forming composition. The hydrogel-forming layer is generally formed by drying the color-changing composition through solvent evaporation. The hydrogel-forming layer is generally thinner and film-like in relation to the thickness of the substrate. Because the color-changing compositions of the invention are liquid or are liquid suspensions at room temperature, they can be applied through printing or stamping directly onto the substrate (thereby self-forming the hydrogel-forming layer). The hydrogel-forming composition may include either a charged, hydrogel-forming polymer and/or charged particles. When a neutral hydrogel-forming polymer is used in the composition, at least one charged polymer or charged particle is also included in the hydrogel-forming composition. The hydrogel-forming composition can also include a combination of a charged, hydrogel-forming polymer and a neutral hydrogel-forming polymer.

The color-changing materials and color-changing compositions of the invention also include a charged colorant that functionally acts as a pH indicator. When the hydrogel-forming composition includes a charged particle, the charged colorant is non-diffusively immobilized on the charged particle. The charged colorant is "non-diffusively immobilized" on the charged particle when the presence of the charged colorant can be reproducibly measured and when the charged colorant is present in sufficient amount to effectuate a change in color visible to the unaided human eye when the color-changing material or color-changing composition is exposed to a pH change (where the pH change would be sufficient to cause a change in color for the charged colorant by itself). The charged colorant may be a neutral pH indicator, a charged pH indicator or a zwitterionic pH indicator. When the hydrogel-forming composition includes a charged particle, the charged colorant may be physically absorbed through hydrophobic interactions or charge-charge interactions. The charged colorant is desirably oppositely charged to the charged particle for immobilization.

As a pH indicator, the charged colorant desirably has a color transition pH at either greater than 9.5 or lower than 5.5. The color change may be from color to colorless, colorless to color or from one color to another color. The charged colorant has the charged functional groups either in the core chromophore structure or derivatized as pendent groups of a polymer. Examples of suitable charged colorants include the following: gentian violet (methyl violet), leucomalachite green, methyl yellow, bromophenol blue, Congo red, methyl orange, malachite green, brillian green, crystal violet, erythrosin B, methyl green, methyl violet 2B, picric acid, napthol yellow S, quinaldine red, Eosin Y, basic fuchsin, 4-(p-anilinophenylazo)benzene-sulfonic acid, sodium salt, phloxine B, bromochlorophenol blue W.S., ethyl orange, bromocresol nile blue A, thymolphthalein, aniline blue W.S., alizarin yellow GG, morgant orange I, tropaeolin O, orange G, acid fuchsin, thiazol yellow G, indigo carmine, phenolphthalein, thymolphthalein, alizarine yellow R, bromocresol green and their respective derivatives. The color-changing materials and color-changing compositions of the invention include a charged colorant in an amount of from 0.05% to 10% of the total weight of the color-changing material or color-changing composition. Desirably, the color-changing materials and color-changing compositions of the invention include a charged colorant in an amount of from 0.5% to 5% of the total weight of the color-changing material or color-changing composition. The color-changing materials and color-changing compositions of the invention may include more than one charged colorant. One or more charged colorants that have visually different colors may be combined or charged colorants having the same visual color may be combined.

In addition to the other components, the color-changing materials and color-changing compositions include a pH adjuster. The pH adjuster is any molecule or composition that may be used to control the pH of the color-changing material or color-changing composition. The pH adjuster may be an acid, a base or a combination of both such as would be found with a buffering composition. The pH adjuster is selected in conjunction with the choice of charged colorant to be used in the color-changing material or color-changing composition. For example, if the color-changing material or color-changing composition includes a charged colorant that has a color transition point that occurs at a pH of lower than 5.5, the selected pH adjuster is desirably an acid to make the pH of the color-changing material or color-changing composition acidic. If the color-changing material or color-changing composition includes a charged colorant that transitions color at a pH higher than 9.5, the selected pH adjuster is desirably a base to make the pH of the color-changing composition basic. Examples of suitable acid pH adjusters include organic acids, inorganic acids and polymeric acids; more specifically, examples include citric acid, oxalic acid, tartaric acid, salicylic acid, palmitic acid and stearic acid. Examples of suitable base pH adjusters include organic bases, inorganic bases and polymeric bases; more specifically, examples include sodium hydroxide, sodium carbonate, sodium bicarbonate, sodium borate, potassium hydroxide, polymeric amines, dendrimeric amine and 1,3-pentanediamine. Combination pH adjusters that have a buffering effect include acetic buffer, borate buffer and carbonate buffer. Desirably, the pH of the combination pH adjuster is either greater than 10 or lower than 5. Typically, the combination pH adjuster is in solution form and the concentration of the buffer may range from about 0.01 milliMolar to about 1000 milliMolar and desirably range from about 1 milliMolar to about 20 milliMolar, depending on the combination pH adjuster selected. The color-changing materials and color-changing compositions of the invention include a pH adjuster in an amount of from 0.001% to 10% of the total weight of the color-changing material or color-changing composition. Desirably, the color-changing material and color-changing compositions of the invention include a pH adjuster in an amount of from 0.1% to 5% of the total weight of the color-changing material or color-changing composition.

Benefits of the pH adjuster include stabilizing the charged colorant against premature color changes that may be caused by exposure to humid environments. For example, the pH adjuster is believed to maintain a stable pH, such as a low pH environment with an acidic pH adjuster, around the charged colorant even when the color-changing material and the hydrogel-forming layer of the multiple-component material are exposed to high humidities.

The color-changing materials and color-changing compositions of the invention may also include a base material. The base material may be a small molecule, a polymeric material or a mixture of small molecules and polymers. Examples of suitable small molecule base materials include glycols, including triglycerols and their derivatives. Examples of suitable polymeric materials that may be used as base materials include polyvinyl alcohol, polyvinyl pyrrolidone, polyethylene glycol, water-soluble derivatives of polyacrylates and polyacrylamides, poly(hydroxyethyl methacrylates), poly(hydroxylethyl acrylates), carboxymethyl cellulose, gelatin and gum Arabic. Another suitable base material for the color-changing materials and color-changing compositions of the invention is a varnish base such as a nitrocellulose compound based varnish or a phenolic-modified co-solvent-type polyamide resin-based varnish. The color-changing materials and color-changing compositions of the invention may include a base material in an amount of from 1% to 50% of the total weight of the color-changing material or color-changing composition. It is believed that the base material may help the stability of the color-changing materials and color-changing compositions, such as by increasing the stability of the suspension of the charged particles, when the hydrogel-forming composition includes charged particles. It is also believed that the base material may improve the adhesion of the color-changing composition to the substrate of the multiple-component material. The base material may be water-soluble or water-insoluble while the charged particles are water-insoluble.

The color-changing materials of the invention include a volatile solvent in addition to the hydrogel-forming composition, the charged colorant and the pH adjuster. With respect to the multiple-component materials of the invention, the components of the color-changing composition may be formed as the hydrogel-forming layer on the substrate. In this form, the components of the color-changing composition must first be dissolved or suspended in a solvent that later evaporates. The result of the color-changing composition forming a hydrogel-forming layer on the substrate is the multiple-component material of the invention. For both the color-changing materials and the color-changing compositions of the invention, the volatile solvent may be a single solvent or a mixture of solvents. Suitable solvents include water, ethanol, methanol, butanol, propanol, acetone, tetrahydrofuran and the mixture of them. In making the color-changing materials and color-changing compositions of the invention, the components may either be dissolved all together in the solvent(s) or sequentially dissolved to make homogenous solutions. When the color-changing materials and color-changing compositions include a charged particle, the charged particles may be suspended in the volatile solvent.

An example of a useful application of the present invention is to apply the color-changing composition to a substrate that is used as a component of a disposable absorbent article. More specifically, the substrate may be a material that is used to form the outer cover of a disposable diaper. The substrate includes a polyolefin film such as polyethylene film or polypropylene film that is used to form the outer cover of a disposable diaper. The hydrogel-forming layer of the present invention may be formed on the substrate. Because the color-changing compositions of the present invention are liquid at room temperature, they can be easily applied through printing to a substrate. Because the outer cover of an absorbent article, such as a disposable diaper, is typically adjacent to the absorbent structure of the article, the color-changing composition is applied to a component that is in proximity to the absorbent structure when the finished product is in use. Therefore, the color-changing composition can be used to indicate a change in condition of the absorbent structure, such as wetness. The color-changing compositions of the invention are water-wettable so that urine can penetrate through the hydrogel-forming layer to cause the structural and environmental change of the hydrogel-forming layer which triggers a rapid color change of the charged colorant component. Yet, the hydrogel-forming layer is water-insoluble to prevent leaching of the charged colorant. These are desirable performance attributes. The hydrogel-forming layer may include other components in addition to the color-changing composition.

In another aspect, the present invention relates to a method of printing on a substrate. The substrate may be a porous foam, a reticulated foam, cellulose tissues, a plastic film, a woven material or a nonwoven material. The method includes a step of providing a substrate to be printed upon. The substrate may be useful by itself or as a component of another useful article, such as an absorbent article. The method also includes a step of applying an ink material onto the substrate. The ink material includes a hydrogel-forming composition, a charged colorant, a pH adjuster and a solvent. The ink material is liquid at room temperature and therefore, the ink material may be applied to the substrate at room temperature. The ink material may be applied onto the substrate in one or more patterns selected from stripes, dots, geometric shapes, irregular shapes, alpha-numeric characters, anthropomorphic images, pictorial representation of animals, pictorial representation of inanimate objects, cartoon characters, logos and trademarks. The ink material may be applied by brush, printing nozzle or stamp.

The following are examples that illustrate aspects of the present invention:

Example 1

20 mg of hydrogel-forming polymer, Amaze XT from AkzoNobel, 4 mg of methacrylamide propyltrimethylammonium chloride, 0.5 ml of 10 mg/ml oxalic acid and 1 ml of 2 mg/ml bromocresol green were added with 2 ml water and 2 ml ethanol to form a mixture. The mixture was applied by spreading onto a piece of outer cover material from a disposable diaper. The outer cover material was a laminate of a spunbond nonwoven material and a polyethylene film. The composition was applied onto the polyethylene film. After the compositions were applied, they were allowed to dry for 60 minutes. The composition remained yellow in color as it dried. The composition adhered well to the outer cover material and did not crack as it dried. When PBS buffer solution was applied to the outer cover materials having the compositions, an instant color change from yellow to blue was observed. The intensity of the blue color increased as the PBS buffer solution was absorbed.

Example 2

Two color-changing materials were prepared and their re-gellation, color change and dye leaching were assessed upon exposure to phosphate buffered saline. While the hydrogel-forming composition components were sampled from commercially-available hair gel products, when they were combined with a charged colorant, pH adjuster and aqueous solvent, they represented color-changing materials of the invention. About 1 milliliter samples of each of the hydrogel-forming compositions (derived from commercially-available hair gel products) were added to an eppendorf vessel and mixed with 100 microliters of a combination of bromocresol green (0.2 mg/mL) and citric acid (5 mg/mL) in water solution. Each representative color-changing material was yellow in color and was applied to the outer cover material of a disposable diaper and left overnight to dry. The color-changing materials formed thin films on the outer cover material and remain yellow. Each film was then exposed to phosphate buffered saline (PBS) buffer. The third column of the table below describes the observations for each film layer that was formed with respect to re-gellation, color change and dye leaching upon contact with PBS buffer.

| Hair gel brand/Company | Hydrogel-Forming Polymers | Observations |
|---|---|---|
| Set Me Up/ Herbal Essences | Acrylate/Beheneth-25 methacrylate copolymer and Acrylate copolymer | Re-gelled, from yellow to deep blue, minimal leaching |
| Frizz-Ease/John Frieda Collection | Copolymer of vinyl acetate & vinyl-pyrrolidone | Re-gelled, from yellow to deep blue, no leaching |

The color-changing materials described and evaluated above show that color-changing materials and color-changing compositions of the invention are capable of dramatic color change upon wetting, minimal dye leaching and the ability to form a film-like layer on a polyolefin sheet.

Example 3

A color-changing material of the invention was prepared by combining 9.6 grams of hair gel, Set Me Up from Herbal Essences (hydrogel-forming composition), 5 milliliters of 40 mg/mL citric acid and 4 milliliters of 0.2 mg/mL bromocresol green. The color-changing material was spread on a piece of polyethylene film, such as would be used as a component of an outer cover of a disposable absorbent article. The color-changing material was allowed to dry at room temperature. The resulting multiple-component material (the combination of the color-changing material on the polyethylene film) was used to replace a section of outer cover film on a HUGGIES disposable diaper (newborn size). The side with the color-changing composition was positioned directly against the absorbent core of the disposable diaper and held in position using tape. The disposable diaper was then insulted with 10 milliliters of PBS buffer solution. After ten minutes, the color-changing composition changed color from greenish yellow to blue in response to the wetness. After one day, there was no visible leaching of the color away from the outer cover into the absorbent core. The strong blue color remained three days later.

While the color-changing materials and multiple-component materials of the invention have been described in detail with respect to specific aspects thereof, it will be appreciated that those skilled in the art, upon attaining an understanding of the foregoing, may readily conceive of alterations to, variations of and equivalents to these materials. Accordingly, the scope of the present invention should be assessed as that of the appended claims and any equivalents thereto.

We claim:

1. A color-changing material comprising:
   a hydrogel-forming composition containing a charged colorant;
   a charged species configured to bind with the charged colorant at multiple pH levels;
   a pH adjuster; and
   a volatile solvent
   wherein the color-changing material is a liquid at room temperature.

2. The color-changing material of claim 1, wherein the color-changing material includes 5 to 50% of the hydrogel-forming composition, 0.1 to 10% of the charged colorant, 0.001 to 10% of the pH adjuster and 50 to 90% of the volatile solvent.

3. The color-changing material of claim 1, wherein the hydrogel-forming composition comprises a charged hydrogel-forming polymer.

4. The color-changing material of claim 1, wherein the hydrogel-forming composition comprises a neutral hydrogel-forming polymer and at least one of a charged polymer or charged particle.

5. The color-changing material of claim 1 further comprising a base material selected from a glycol, a polymeric material and a combination thereof.

6. The color-changing material of claim 4, wherein the neutral hydrogel-forming polymer is selected from polyethylene oxide, polyAMPS, polyvinylpyrrolidone, polyacrylamide, polyvinyl alcohol, sodium polyacrylate, agarose, methylcellulose and hylaronan.

7. The color-changing material of claim 1, wherein the color-changing material includes more than one charged colorant.

8. The color-changing material of claim 1, wherein the charged colorant is a pH indicator having a color transition pH of greater than 9.

9. The color-changing material of claim 1, wherein the charged colorant is a pH indicator having a color transition pH of less than 5.5.

10. The color-changing material of claim 1, wherein the volatile solvent is selected from water, low alcohol, acetone, tetrahydrofuran and mixtures of these volatile solvents.

11. A multiple-component material, the material comprising:
    a substrate, the substrate having a hydrogel-forming film, wherein the hydrogel-forming film includes a color-changing composition, the color-changing composition comprising
    a hydrogel-forming composition containing a charged colorant;
    a charged species configured to bind with the charged colorant at multiple pH levels; and
    a pH adjuster.

12. The multiple-component material of claim 11, wherein the hydrogel-forming composition comprises a charged, hydrogel-forming polymer.

13. The multiple-component material of claim 11, wherein the hydrogel-forming composition comprises a neutral, hydrogel-forming polymer and at least one of a charged polymer or a charged particle.

14. The multiple-component material of claim 11, wherein the hydrogel-forming film is formed on the substrate in one or more patterns selected from stripes, dots, geometric shapes, irregular shapes, alpha-numeric characters, anthropomorphic images, pictorial representation of animals, pictorial representation of inanimate objects, cartoon characters, logos and trademarks.

15. A disposable absorbent article including the multiple-component material of claim 11.

16. The multiple-component material of claim 11, wherein the multiple-component material is an outer cover material for a disposable absorbent article.

17. The multiple-component material of claim 11, wherein the color-changing composition includes more than one charged colorant.

18. The multiple-component material of claim 11, wherein the substrate is a non-woven material.

19. The multiple-component material of claim 11, wherein the substrate is a polyolefin film.

20. The multiple-component material of claim 19, wherein the polyolefin film is selected from a polyethylene film and a polypropylene film.

21. A method of printing on a substrate, comprising the steps of:
    providing a substrate to be printed upon; and
    applying a liquid ink material onto the substrate, wherein the liquid ink material includes a hydrogel-forming composition including at least one charged species, a charged colorant, a pH adjuster and a volatile solvent; and
    wherein the liquid ink material is applied to the substrate at room temperature.

22. The method of claim 21, wherein the liquid ink material is applied onto the substrate in one or more patterns selected from stripes, dots, geometric shapes, irregular shapes, alpha-numeric characters, anthropomorphic images, pictorial representation of animals, pictorial representation of inanimate objects, cartoon characters, logos and trademarks.

* * * * *